(12) United States Patent
Kamatchi

(10) Patent No.: US 10,660,482 B2
(45) Date of Patent: May 26, 2020

(54) INTELLIGENT DISPENSER OF DISINFECTANT GEL FOR CONNECTION TO DISINFECTION HABITS MONITORING SYSTEM

(71) Applicant: Rajaram Govindarajan Kamatchi, Barcelona (ES)

(72) Inventor: Rajaram Govindarajan Kamatchi, Barcelona (ES)

(*) Notice: Subject to any disclaimer, the term of this patent is extended or adjusted under 35 U.S.C. 154(b) by 4 days.

(21) Appl. No.: 15/983,273

(22) Filed: May 18, 2018

(65) Prior Publication Data
US 2018/0364672 A1  Dec. 20, 2018

(30) Foreign Application Priority Data
Jun. 16, 2017  (ES) .............................. 201730724 U

(51) Int. Cl.
*A47K 5/12*  (2006.01)
*A61L 2/22*  (2006.01)
(Continued)

(52) U.S. Cl.
CPC ............ *A47K 5/1217* (2013.01); *A01N 25/04* (2013.01); *A61L 2/18* (2013.01); *A61L 2/22* (2013.01);
(Continued)

(58) Field of Classification Search
CPC .. G08B 21/245; G16H 40/20; G07C 9/00111; A47K 5/1217; A61L 2/24
See application file for complete search history.

(56) References Cited

U.S. PATENT DOCUMENTS

| 5,842,608 A | * | 12/1998 | Buchler | .................. A47K 5/12 222/181.3 |
|---|---|---|---|---|
| 5,945,910 A | | 8/1999 | Gorra | |

(Continued)

FOREIGN PATENT DOCUMENTS

| DE | 102012105365 A1 | * | 12/2013 |
|---|---|---|---|
| GB | 2534363 A | | 7/2016 |

OTHER PUBLICATIONS

Notification of Transmittal of the International Search Report and the Written Opinion of the International Searching Authority dated Sep. 11, 2018, in connection with corresponding international Application No. PCT/IB2018/053470 (23 pgs.).

(Continued)

*Primary Examiner* — Crystal J Barnes-Bullock
(74) *Attorney, Agent, or Firm* — Maier & Maier, PLLC

(57) ABSTRACT

Intelligent dispenser of disinfectant gel for connection to disinfection habits monitoring system that includes a disinfectant gel dispenser, a user recognition device and an electronic device. The dispenser also includes a communicator device to transmit at least the user identification data and dispenser identification data to a computing device member of a disinfection habits monitoring system. The computing device can process the transmitted user identification data linking them to the individual dispenser transmitter of the identification data, permitting to determine the disinfection habits of each user individually, and the computing device can transmit to an information emitter information related with the users identified by the recognition device and information relevant to tasks performed or omitted by the users and/or in accordance with the sanitation protocols, or area information corresponding to the physical position of the individual dispenser.

13 Claims, 2 Drawing Sheets

(51) Int. Cl.
*A61L 2/18* (2006.01)
*G08B 21/24* (2006.01)
*G16H 40/20* (2018.01)
*A61L 2/24* (2006.01)
*A01N 25/04* (2006.01)
*G05B 19/05* (2006.01)
*H04W 4/38* (2018.01)
*H04W 4/80* (2018.01)
*H04W 84/12* (2009.01)

(52) U.S. Cl.
CPC ............ *A61L 2/24* (2013.01); *G05B 19/05* (2013.01); *G08B 21/245* (2013.01); *G16H 40/20* (2018.01); *G05B 2219/15117* (2013.01); *G05B 2219/23026* (2013.01); *G05B 2219/2633* (2013.01); *H04W 4/38* (2018.02); *H04W 4/80* (2018.02); *H04W 84/12* (2013.01)

(56) References Cited

U.S. PATENT DOCUMENTS

| | | | |
|---|---|---|---|
| 7,605,704 B2 | 10/2009 | Munro et al. | |
| 8,061,350 B2* | 11/2011 | Boeck | F04B 53/16 128/200.14 |
| 8,237,558 B2* | 8/2012 | Seyed Momen | G01S 1/70 340/539.11 |
| 9,433,695 B2 | 9/2016 | Aamodt et al. | |
| 9,972,193 B2* | 5/2018 | Laufer | G08B 21/245 |
| 10,223,894 B2* | 3/2019 | Raichman | G08B 21/245 |
| 10,332,382 B2* | 6/2019 | Thyroff | G08B 21/24 |
| 2006/0227653 A1* | 10/2006 | Keller | A61B 17/00491 366/139 |
| 2008/0131332 A1 | 6/2008 | Nguyen et al. | |
| 2009/0195385 A1* | 8/2009 | Huang | G08B 21/245 340/572.1 |
| 2009/0219131 A1* | 9/2009 | Barnett | G16H 40/20 340/5.2 |
| 2014/0333744 A1* | 11/2014 | Baym | G08B 21/245 348/77 |

OTHER PUBLICATIONS

M. Akif Meydanci, et al., "RFID Based Hand Hygiene Compliance Monitoring Station", IEEE International Conference on Control System, Computing and Engineering, Nov. 29-Dec. 1, 2013, Penang, Malaysia, pp. 573-576 (4 pgs.).

Malak Baslyman, et al., "Real-time and location-based hand hygiene monitoring and notification: proof-of-concept system and experimentation", Pers Ubiquit Comput, vol. 19, 2015, pp. 667-688 (22 pgs.).

A.I. Levchenko, et al., "Distributed IR based technology to monitor hand hygiene of healthcare staff", Science and Technology for Humanity (TIC-STH), 2009 IEEE Toronto International Conference, Piscataway, NJ, USA, Sep. 26, 2009, pp. 252-255 (4 pgs.).

* cited by examiner

INTELLIGENT DISPENSER OF DISINFECTANT GEL FOR CONNECTION TO DISINFECTION HABITS MONITORING SYSTEM

FIELD

The present invention relates to an intelligent dispenser of disinfectant gel for connection to disinfection habits monitoring system, said dispenser being intended mainly, but without restriction, to be installed in sanitary facilities such as hospitals or outpatient clinics for the correct and frequent disinfection of the health personnel, avoiding the transmission of infectious diseases among patients or the health personnel themselves. It is intended that this invention may also be used in food processing and distribution facilities or in pharmaceutical industries to avoid the transmission of infectious diseases to consumers by the staff involved.

BACKGROUND

Dispensers of disinfectant gel are known, that dose amounts of disinfectant gel allowing a quick and efficient disinfection of hands without requiring the use of water, soap or means for a subsequent drying of the hands, that could produce a new contamination of the hands.

Usually, these are wall-mounted dispensers that include a push button, which provides a dose when being pressed or otherwise. However, this known solution does not allow control over who, when and how many times the hands have been disinfected, preventing monitoring and correction of reckless attitudes in what disinfection is concerned, this aspect being especially relevant in hospitals or geriatric environments, where the infections can be transferred among patients unintentionally by the health personnel, by not correctly conducting the disinfection at the appropriate moments.

There are known dispensers that allow the recording and identification of the user of the dispenser. U.S. Pat. No. 5,945,910 discloses a method and apparatus for monitoring and reporting the hand washing habits of users working in various environments in which the apparatus, being essentially a soap dispenser, is located. US2008131332 discloses a dispenser system equipped with a subsystem for wirelessly detecting the presence and identity of a user and the use of the dispenser by said user, registering said user identity. U.S. Pat. No. 7,605,704 discloses a system consisting of several dispensers, user detectors and data emitters, such detectors being able to identify the users of the dispensers by different means, such as biometric identification or wireless identification cards with which the users are equipped and communicating the user identities and the receipt of disinfectant gel by the dispensers, to a central computer which registers such data.

Dispensers of disinfectant gel that simply dispense gel do not allow for the user of the dispenser to receive additional information related to the facility/area in which the dispenser is located and the disinfection requirements associated to said facility/area. For example, in a hospital environment if the user is a member of the hospital health personnel, such as a medical doctor, and is using a dispenser located within the room where a patient is hospitalized, it is useful if upon identification of the user receiving the disinfectant gel from the dispenser, the user also receives from the dispenser information related to the medical file of the patient, such information being potentially relevant to the need for an adequate disinfection before and after the user interacts with the patient.

Automatic soap dispensers are also known, that automatically provide a dose of soap when detecting the presence of a hand.

None of the aforementioned known dispensers of disinfectant gel allows for simultaneously monitoring of the disinfection habits of the user while being able to provide said user with user customized information relevant to the individual needs of the user and habits for being able to be adequately disinfected and adequately perform their duties.

SUMMARY

The present invention relates to an automatic dispenser of disinfectant gel.

It will be understood that said disinfectant gel will be a product with bactericidal properties and that will preferably be a product of rapid evaporation, such as for example products with an alcohol base, avoiding having to dry the hands after disinfection.

The proposed dispenser includes a casing that supports:
at least one reservoir of disinfectant gel;
a dispensing nozzle of disinfectant gel connected to said reservoir of disinfectant gel;
a dosing device connected to said reservoir and/or to said dispensing nozzle and configured to dispense a predefined amount of disinfectant gel through said dispensing nozzle;
an actuator device connected to the dosing device for its actuation producing the dispensation of said predefined amount of disinfectant gel;

Thus, the actuator device allows the dosing device to be actuated, which ensures that the amount of disinfectant gel dosed is always the same and that it is a sufficient amount for an effective disinfection. The disinfectant gel is dosed from at least one reservoir through the dispensing nozzle.

Said dosing device can be of very different natures, for example it may consist of a piston housing of a predefined dimension that is filled with disinfectant gel after each dispensation and that when the actuator device is operated collapses and empties through the dispensing nozzle. Alternatively, the dispensation can be produced by compressing, in a controlled manner, by means of a pressure surface, the reservoir which is flexible reducing its volume in a controlled manner causing the exit of a regulated amount of disinfectant gel. Other embodiments may contemplate introducing air under pressure into the container and/or regulating by a valve the opening and closing of the dispensing nozzle in a controlled manner to regulate the flow of dispensed disinfectant gel, said valve being actuated by the actuator device.

The present invention proposes that the dispenser further includes:
a user recognition device which collects user identification data, in each dispensation; and
an electronic device connected to said user recognition device;
characterized in that the dispenser also includes a communicator device connected to said electronic device, to transmit at least the user identification data and dispenser identification data to a computing device member of a disinfection habits monitoring system and receive information from said computing device; wherein
said computing device can process said transmitted user identification data linking them to the individual dispenser transmitter of said identification data through the dispenser identification data, differentiating said user identification data from other identification data of other users transmitted from other dispensers, permitting to determine the disinfection habits of each user individually; and said computing device can transmit to an information emitter, through said communicator device in connection with said electronic device, information related with the users identified by the said recognition device and information relevant to tasks performed or omitted by said users and/or in accordance with the sanitation protocols, or area information corresponding to the physical position of the individual dispenser, identified by the dispenser identification data, and included in a database accessed by said computing device.

It will be understood that an electronic device will be a device that will integrate a memory and with a necessary computing power to execute automation and/or control functions. Examples of an electronic device may be a programmable logic controller, a computer or another similar device. It is also contemplated that said electronic device is local, partially or totally remote with respect to the dispenser.

Thus, the proposed dispenser will permit to identify a user by means of the user recognition device integrated in the dispenser, allowing a precise control of when and to whom disinfectant gel has been supplied from a specific dispenser.

Preferably the dispensation of disinfectant gel is not restricted only to users which have been identified through the user recognition device, thus allowing every user who requires it to be provided with a dose of disinfectant gel, however it is considered that the regular users will have the incentive to identify themselves to obtain a favourable record of disinfection habits.

It is contemplated however, as an alternative possibility, that the dispenser provides disinfectant gel only to identified users.

It is proposed that the dispenser can further include a clock connected to the electronic device and that the electronic device is also configured to further transmit temporary data linked to the user identification data. This will allow a more precise record of the moment in which each dispensation has been made to each individual user. This embodiment would allow the dispenser to store the data together with the temporary record, allowing the data to be sent to the computing device in real time or at different times other than the dispensation time, thus reducing the electrical consumption of the device by making said communication only every so often.

According to another embodiment, the dispenser is anchored in a physical position, and the dispenser identification data are linked to data related to said physical position of the dispenser, for example by means of a database that relates both parameters, said database being stored in the computing device, thus allowing to link the user data transmitted by said dispenser with said physical position of the dispenser. That is, the system is able to know the position of each individual dispenser by means of a register stored in its memory, and when information regarding a dispensation of disinfectant gel made by an individual dispenser to a specific user is received, the system also knows the physical position in which said dispensation has been conducted. This allows for example to know if a user is properly sanitized when accessing an area that requires said disinfection, such as a patient room, an operating room, etc.

According to an alternative embodiment it is proposed that the user recognition device can be a biometric detector with a fingerprint reader that ingrates a finger scanning surface; or a device for facial recognition, recognition of the shape of the retina or iris; or a device for recognizing the geometry of the hand, or a voice recognition device.

In all cases, dispensation can take place even if the recognition device cannot identify a user, and subsequently all information, such as the biometry of the new unidentified user, how many times such unidentified users were dispensed gel, and from which dispenser devices, at what time and how many times each dispensation occurred, can be transmitted to the monitoring system.

In the first case of the fingerprint reader device, the user should place a finger on said finger scanning surface to identify himself, detecting the identifying patterns of his fingerprint. In the second example, relating to a facial, retinal or iris recognition device, it would be sufficient for the user to stand in front of the dispenser, for example detecting, by means of a camera integrated in the dispenser, an image of the face or of the eye of the user that, after its analysis, would allow to identify said user from the shape, position and size of the distinctive elements of the part of the analysed anatomy.

In the third example of a device for recognizing the geometry of the hand of the user, it would be sufficient for the user to place a hand under the dispenser, a camera or another sensor of said dispenser being focused on that area, capturing an image or information relating the geometry of the hand that, by its analysis, would allow to identify the user by means of the measurement of the size, thickness, proportions, etc. of the fingers, the palms or its joints. In this last example, the camera or sensor can be adjacent to the dispensing nozzle, so that the position of the hand for the biometric identification and for the reception of the dose of the disinfectant gel is the same.

Finally, in a fourth embodiment, a voice recognition device, which will integrate a microphone, will allow the dispenser to detect the voice of the user and, by its analysis, determine the identity of the user.

It is also expected that the user is bearer of an identifier device that emits an identifying signal when in proximity to a dispenser, that in such case will have an antenna adapted for this purpose. Said identifying device can be both an active emitter and a passive emitter device that interacts with certain signals in proximity to the emitting source of the same.

It is proposed that the user recognition device can be an identifier device selected from an identification card reader, whether magnetic, contact, proximity, RFID cards, by reading a code such as a barcode or QR, by means of a proximity detector of personal identification cards, chips or antennas, such as EM card, Mifare technology cards, or other present or future technologies that can be available in the market for the identification of people. It is also contemplated the identification by means of a personal identification code insertion keypad, that allows the user to identify himself by inserting a personal identification code using said keypad.

The information obtained through said user recognition device will be transmitted by a communicator device connected to said electronic device. Preferably said communicator device will be a wireless communicator device, such as for example a device based on the WIFI protocol, Bluetooth, or another radiofrequency signal. The emitted data will be captured by a computing device that centralizes all the information emitted by multiple dispensers distributed over a hospital, sanitary or geriatric facility or food processing and/or distribution facilities or pharmaceutical industries, for example. It will be understood that the computing device will preferably be a computer or programmable logic controller.

If there is any instantaneous interruption for transmitting the user identification information because of wi-fi failures, or of other reasons, the dispenser device will store the information temporarily and when the connection is available will transmit it to the monitoring system.

This allows to have a centralized record of the use that every registered user makes of each dispenser, and also allows to integrate a network of dispensers centralizing all the information and conducting statistics and monitoring. This can be especially useful in hospitals where a central computer can contain a record of all the medical personnel and of the patients assigned to each of the persons comprising the medical personnel, thus allowing that multiple dispensers of disinfectant gel installed in the hospital to supply said computer with data regarding which user uses which dispenser of disinfectant gel and when he uses it, thus allowing to check if the disinfection protocols of the registered personnel are correctly fulfilled, and allowing to detect dysfunctions and to introduce improvements.

Obviously, the computing device can also emit signals to the dispensers, such as for example a signal related to the users who are registered in the system.

According to another preferred embodiment the dispenser device further includes a battery that powers at least said electronic device, said recognition device and said communicator device. This allows the dispenser to be autonomous and to be installed anywhere without requiring an electrical supply installation. In that case the battery should be recharged or substituted periodically, just like the disinfectant gel of the reservoir. Preferably, when said battery is near exhaustion the dispenser will emit a warning signal, either through the communicator device, either by means of a light indicator integrated in the dispenser itself.

The dispenser can have, in accordance with another embodiment, two reservoirs of disinfectant gel and can be configured so that when one of the reservoirs is depleted the electronic device generates a warning signal and the dispensation from the other reservoir is initiated.

The warning signal can be for example a light signal emitted by a LED integrated in the dispenser and/or an acoustic signal emitted by a sound-emitting device integrated in the dispenser and/or an information signal emitted by the communicator device to be communicated to the computing device.

The dispenser may further include a proximity detector adjacent to the dispensing nozzle for the detection of the presence of a user's hands in front of said dispensing nozzle, and where the electronic device is connected to said proximity detector and configured to not activate the actuator device until a detection is produced by said proximity detector.

According to this example a user can be identified in front of the dispenser and, once a positive identification is obtained, that can be indicated for example by means of a light and/or sound indicator, proceed to place the hands in front of the dispensing nozzle said hands being detected by the proximity detector and proceeding then to supply the dose of disinfectant gel avoiding the dispensation of the disinfectant gel in the absence of the hands of the user. According to this embodiment the actuator device will include a motor controlled by the electronic device for an automatic dispensation of the disinfectant gel.

According to an additional embodiment the actuator device is a push button or lever accessible from the exterior of the automatic dispenser mechanically connected to said dosing device, resulting in dispensing as a result of the activation of said push button or lever. In an embodiment it is contemplated that said push button integrates the fingerprint reader device, so that at the time that the user presses said push button his identification is conducted.

Optionally, the electronic device can be connected to a blocking mechanism and configured to block and/or unblock the actuator device depending on the information obtained through the user recognition device.

That is to say that the dispenser includes a push button or lever that, by its action, activates the dosing device producing the supply of a dose of disinfectant gel by action of the movement of said push button or lever to which it is mechanically connected, so that the dispensation to be produced would not require a motor or consumption of electric power. Nevertheless, to avoid that a user obtains a dose of disinfectant gel without before identifying himself, the recognition device would be connected to a blocking mechanism that interferes with said push button or lever, or with the mechanical connection with the dosing device, so that the activation of the push button or lever is only possible or is only transmitted to the dosing device after the correct identification of the user by the biometric sensor, that activates the blocking mechanism liberating said blocking. This solution would require lower energy consumption, facilitating its autonomous installation, and would reduce its cost by not requiring a motor for the supply of the disinfectant gel dose.

Another suggested embodiment contemplates that the dispenser includes an information emitter selected between a lighting signal, a screen or a loudspeaker. Said information emitter device would be in communication with the computing device through the communicator device and controlled by the electronic device, which would be configured to emit, though the information emitter, information related with the user identified by the user recognition device received through the communicator device.

That is to say that, after the identification of the user the dispenser could emit through the information emitter visual or auditory information that is of interest to the aforementioned identified user. Said relevant information would be sent from the computing device that could contain a database from which to extract the relevant information for a specific user. For example, said information could be, in the case of the hospital use of the proposed dispenser, relevant information for a specific doctor identified by the dispenser, and of which the specific location related to the location of the dispenser is known, for example a patient room. This database would therefore allow the computing device, upon receiving the identification of a doctor located in a room, to transmit to him important information related to the patient who occupies said room, such as for example information relative to the medication, to recent events related with said patient, to allergies, to treatments to practise, reminders, etc. Obviously, said information would be adapted to the user identified, since it would not be the same information shown to a doctor than to a nursing assistant, or to a patient, which may or may not be related to patient specific information at the dispensing location retrieved from other computing devices or data bases of the hospital.

Other information of interest that can be transmitted will be the consumption of gel in each dispenser, which is calculated by the system automatically based on the number of dispensations from a new reservoir and the quantity dispensed each time, so that in real time hospital maintenance staff can monitor the consumption patterns of each dispenser based on its location characteristics thus allowing to know when they need to replace or recharge the gel reservoir to ensure gel availability for continued dispensation at each and every dispensation device. The real-time consumption data can also be transmitted to gel vendors to ensure gel supply just-in-time to keep gel stocks at the hospital warehouses at optimum levels.

Said information emitter and information emitted by it to the user of the dispenser, may also be of importance when the dispenser and the associated monitoring system are used in establishments other than health care facilities. For example, when the dispenser and disinfection habits monitoring system are used in facilities where commercial goods, such as pharmaceuticals or food are processed and/or produced under hygienic conditions, the information emitter may emit to the identified user information related to the number of doses of disinfection gel the user should receive, said number of doses being related to the specific task of the user within the facility where the dispenser is located.

For example, in a food industry, if staff do not disinfect their hands after touching non-sterile materials/equipment, or after going to the toilet, the system can detect such non-compliance by comparing the moments tasks were performed by an employee and the moments and places hand hygiene was performed or not. In addition, if breaches are detected, it is possible to isolate batches of affected food products and prevent the distribution of potentially contaminated batches, or if necessary remove those from the shelves of supermarket, to prevent consumers from becoming ill. Another example of the industry with a cleanroom is that of medical devices or medicines, where workers must also strictly comply with hand hygiene protocols to avoid the contamination of medicines and other sanitary products and the monitoring system described can detect lots of products affected by said non-compliance so that the competent authority can be notified and/or generate relevant notices about batches of contaminated medicine in order to prevent them from reaching the market and withdrawing them from the market if they have already been distributed. This relevant information notices about batches may also be emitted to the user by the computing device, through the communicator device in connection with the electric device.

The same idea can even be extended to restaurants where the kitchen staff and waiters have to disinfect their hands every time they have used to toilet to avoid food contamination and such habits can be monitored.

Said information could be transmitted in visual form through a screen, or in auditory form through a loudspeaker.

When the information emitter consists of a lighting signal, depending on the information related with the user identified, may light up in different manner and/or combinations. For example, when the information received is associated with the duty of the user to receive more than one doses of disinfectant gel from the dispenser, the number of doses may be indicated to the user by the number of lights being turned on. For example, if according to protocol, a user has to disinfect twice once before and once after touching a specific patient, after dispensing the "before" doses to a specific user, the display of the dispenser of the same patient location will keep the information in memory and might remind the user that he or she has not yet dispensed the "after" doses, thus allowing for better compliance of the protocol. In another example, the aforementioned number of doses may be indicated by the number of times a certain light of the information emitter turns on in a consecutive manner. In a third example, the aforementioned number of doses or information related to the caution that the user should exhibit for ensuring adequate disinfection of his hands, may be indicated to the user by the colour of the lights of the information emitter that are turned on.

It will be understood that, in spite of being described the invention as applied to the dispensation of disinfectant gel, other equivalent applications will also be protected by the present document. For example, for the dispensation of other liquid substances, such as drinks of any kind, medicines, or even non-liquid hospital supplies, such as gases or others.

Other characteristics of the invention will appear in the following detailed description of an exemplary embodiment.

BRIEF DESCRIPTION OF THE FIGURES

The previous and other advantages and characteristics will be understood more thoroughly from the following detailed description of an exemplary embodiment with reference to the attached drawings, which should be taken as illustrative and non-limiting, in which.

DETAILED DESCRIPTION

The attached figures show exemplary embodiments of the present invention with an illustrative and non-limiting character.

Figure 1:
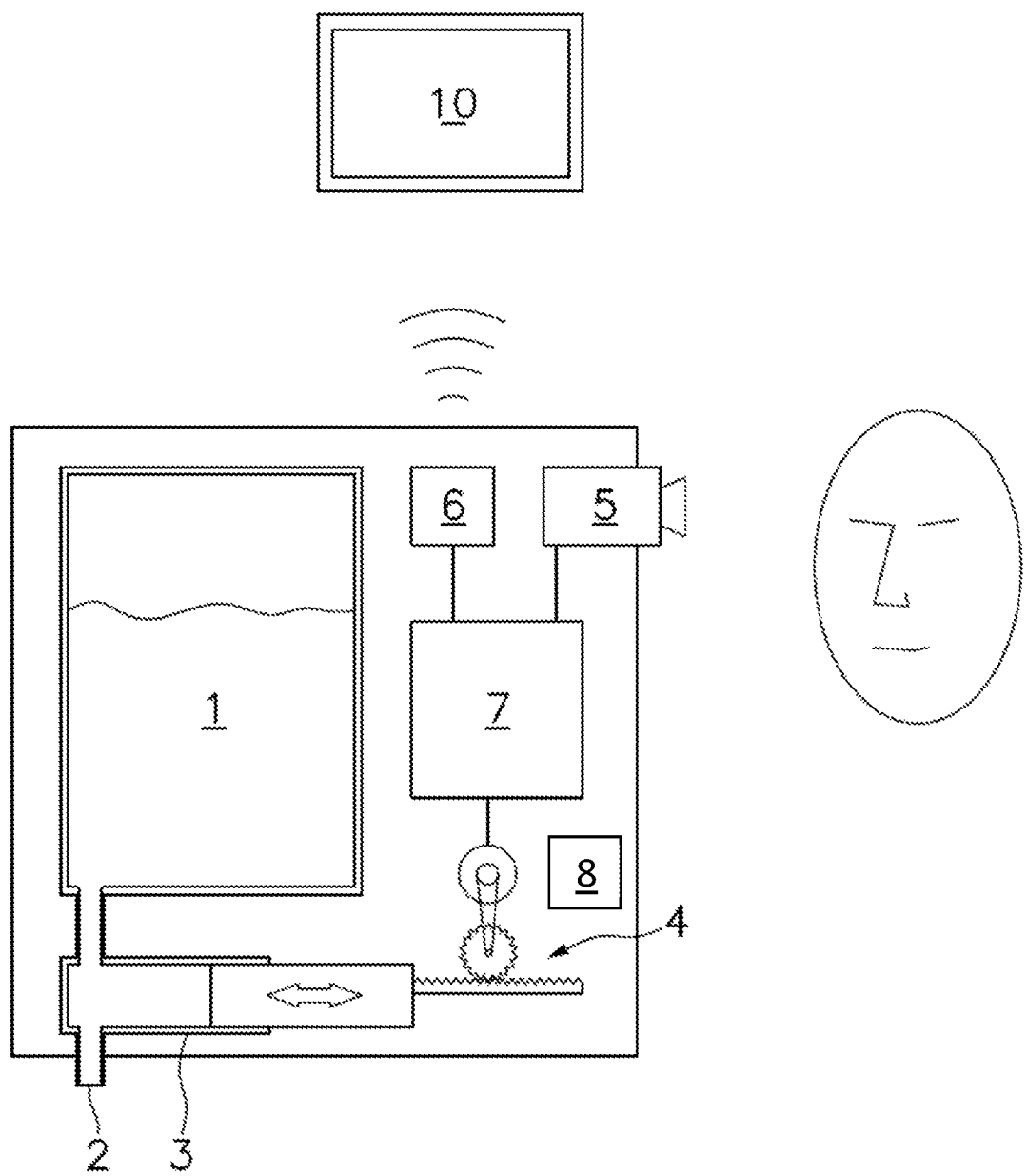
FIG. 1 shows a schematic view of the proposed dispenser according to a first embodiment provided with a facial recognition device and with a motorized actuator device.

The present invention relates to, in agreement with a first preferred embodiment shown in FIG. 1, an intelligent dispenser of disinfectant gel that integrates, inside a casing anchored to a wall, or portable dispensers placed on a table or a trolley, a reservoir 1 of disinfectant gel connected to a dosing device 3 which in turn is connected to a dispensing nozzle 2.

In this embodiment the dosing device 3 consists of a cavity with a capacity equivalent to the amount of disinfectant gel to be dispensed in one dose, said cavity being coupled to a piston that slides within said cavity reducing its volume when expelling the disinfectant gel contained therein.

The piston of the dosing device 3 is connected to an actuator device 4, that in this embodiment is an automatic actuator device formed by an electric motor or servomotor that activates a mechanism that displaces said piston, in this case and only by way of non-limiting example, by means of a pinion geared to a toothed bar connected to the piston. As will be obvious many other distinct embodiments of the mentioned mechanism can be achieved by an expert without this in essence modifying the invention.

The displacement of the piston in one direction will increase the size of the cavity and, with the help of gravity, will introduce an amount of disinfectant gel inside the same from the reservoir 1 located beyond said cavity and connected to the same by a conduit. The disinfectant gel will remain inside the cavity of the dosing device 3 until the actuator device 4 is activated displacing the piston and causing the exit of the disinfectant gel by the dispensing nozzle 2. The density of said disinfectant gel can impede said disinfectant gel from exiting the dispensing nozzle 2 in the absence of activation of the actuator device 4, and gravity can impede the disinfectant gel of the dosing device 3 from going back inside the reservoir 1, nevertheless it is contemplated the possibility of including non-return valves, or elastic valves that impede an undesired circulation of the disinfectant gel, as well as the entry of external air through the dispensing nozzle 2.

As will become obvious many other embodiments of the dosing device 3 different than the ones described herein are possible, as for example the ones described in other parts of this application, or many others, without modifying the essence of the invention.

The proposed dispenser further includes a user recognition device 5, that in this embodiment consists of a camera directed towards an area where the presence of a user's face is expected. Said camera is part of a biometric detector that captures an image of the user's face and delivers it to an electronic device 7, also integrated in the dispenser.

The captured image can be analysed by means of a pattern recognition algorithm that allows identification of the user that appears in the image, said analysis being executed by means of said electronic device 7 and generating user identification data of the user. Preferably, the dispenser will emit an acoustic or light signal when the identification process has occurred correctly.

Subsequently, said identification data can be emitted, together with dispenser identification data stored in the electronic device 7, by a communicator device 6 also connected to the electronic device 7, said send data being captured by a remote computing device 10 that in this case is proposed to be a computer where said data can be stored and analysed.

Alternatively, the electronic device 7 can directly send as identification data the captured image also together with the dispenser identification data, so that said data be captured by the computing device 10, that by means of a pattern recognition algorithm could analyse the received image and conduct the identification of the user shown in the image.

The computing device can subsequently transmit to an information emitter 8 information related with the users identified by the said recognition device and information relevant to tasks performed or omitted by said users and/or in accordance with the sanitation protocols, or area information corresponding to the physical position of the individual dispenser Optionally, the computing device 10 can send a signal to the dispenser to notify that the identification has been completed correctly, so that this can show a signal, for example light or acoustic, and the user has the certainty that he has been correctly identified.

The communicator device 6 will preferably be a radiofrequency signal emitter such as for example a signal according to the WIFI or Bluetooth protocol, or any other present or future technology that may be available for data communication.

Figure 2:
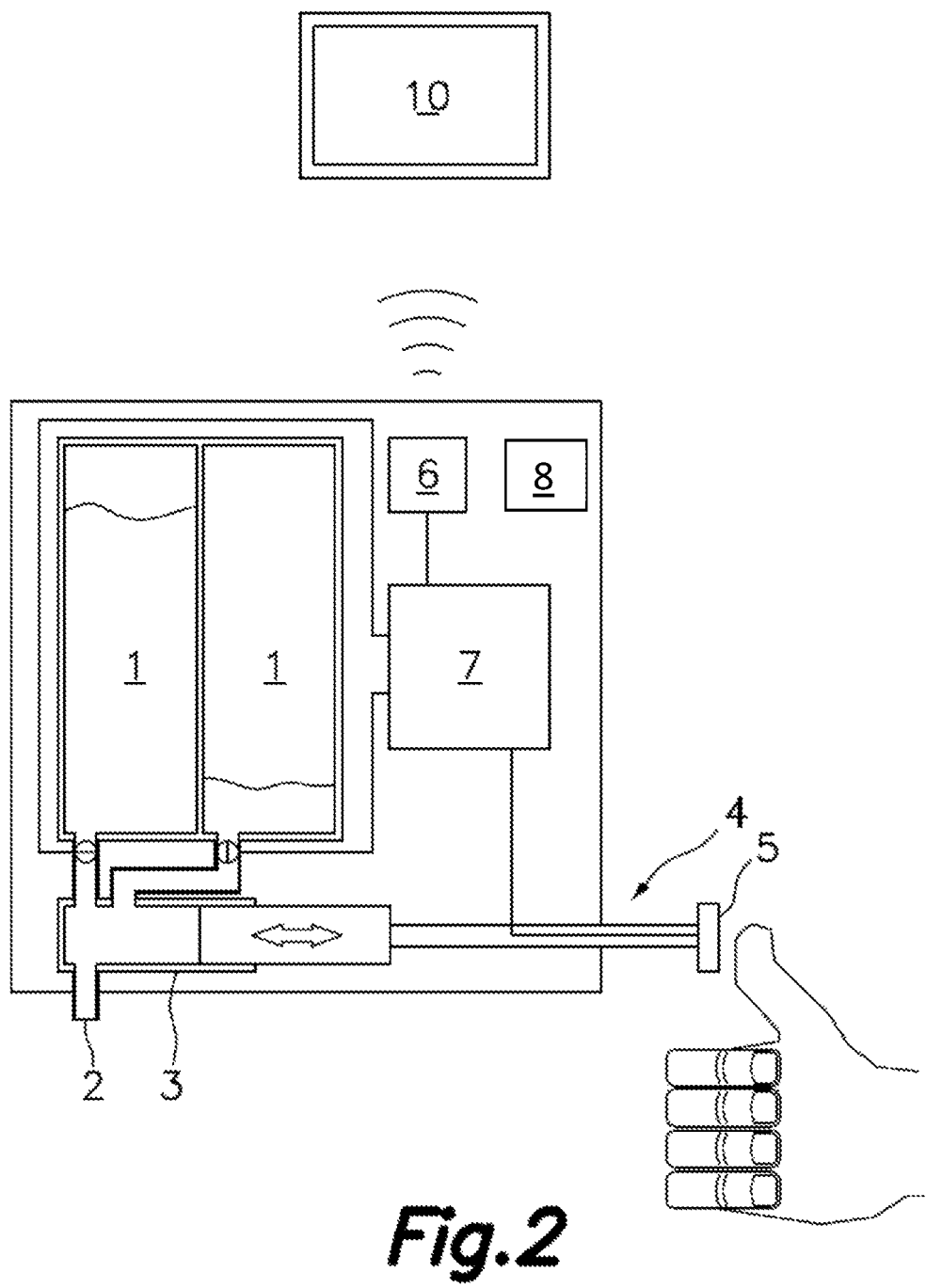
FIG. 2 shows a schematic view of the proposed dispenser according to a second embodiment provided with a fingerprint reader device integrated in the push button that constitutes the actuator device of the dispensation, being the dispenser further provided with two reservoirs.

According to a second embodiment shown in FIG. 2 the dosing device is equal to that described in relation to the first embodiment but is connected to two independent reservoirs 1 by conduits that include a valve controlled through the electronic device 7. This allows said electronic device 7 to connect to the dosing device 3 with one or with the other reservoirs 1 depending on which one is full and which empty. The detection of the emptying of the reservoir can be achieved in very different ways, either by counting the dispensations made from each reservoir, or by sensors such as photosensitive cells, weight sensors, etc. as drain detectors.

When the electronic device 7 determines that a reservoir 1 is empty, it disconnects that reservoir from the dosing device 3, and connects the other reservoir 1 to said dosing device 3 by means of the control of the valves describes above.

In this second embodiment it is contemplated in addition that the actuator device 4 is not automatic, but it is manual by means of a push button connected to the piston of the dosing device 3. Said push button may be pressed at any moment by a user, him being identified or not, producing a dose of disinfectant gel. However, it is proposed that the push button itself can integrate a fingerprint reader device as user recognition device 5, so that at the same time that it is pushed by a user it can produce the reading of his fingerprint.

The obtained data are transmitted to the electronic device 7 that can conduct the analysis of said data for conducting the identification of the user, generating an information that, together with the dispenser identification data, will be transmitted by a communicator device 6 as described in relation to the first embodiment.

Alternatively, the data provided by the fingerprint reader device can be sent unanalysed also through the communicator device 6, together with the dispenser identification data, their analysis being conducted in a remote computing device 10 that receives said data.

In any case, both the first and the second embodiments allow that a remote computing device 10 knows how many times a certain user has utilised a specific dispenser. If a clock is also incorporated, either in the dispenser or in the remote computing device, it can also be determined at what moments said dispensations have been produced. This, together with the dispenser identification data, allows to integrate a plurality of said dispensers inside an enclosure constituting a disinfection habits monitoring system of the users.

Said system will permit to obtain statistics and to monitor the disinfection protocols compliance by each one of the individual members of the personnel of a centre, which allows to detect bad habits and to correct them before undesired infections occur.

It will be understood that the described in an embodiment different parts that constitute the invention can be freely combined with the parts described in other different embodiments even if said combination has not been described explicitly, provided that there is no prejudice in the combination.

The invention claimed is:

1. An intelligent dispenser of disinfectant gel for connection to a disinfection habits monitoring system comprising:
    a casing that supports:
    at least one reservoir of disinfectant gel;
    a dispensing nozzle of disinfectant gel connected to said reservoir of disinfectant gel;
    a dosing device connected to said reservoir and/or to said dispensing nozzle and configured to dispense a predefined quantity of disinfectant gel through said dispensing nozzle;
    an actuator device connected to the dosing device for its actuation producing the dispensation of the predefined amount of disinfectant gel;
    a user recognition device which collects user identification data, in each dispensation; and
    an electronic device connected to said user recognition device,
    wherein the dispenser also includes a communicator device connected to said electronic device, to transmit at least the user identification data and dispenser identification data to a computing device member of the disinfection habits monitoring system and receive information from said computing device;

wherein said computing device can process said transmitted user identification data linking them to the individual dispenser transmitter of said identification data through the dispenser identification data, differentiating said user identification data from other identification data of other users transmitted from other dispensers, permitting to determine the disinfection habits of each user individually;

wherein said computing device can transmit to an information emitter, through said communicator device in connection with said electronic device, information related with the users identified by the said recognition device and information relevant to tasks performed or omitted by said users and/or in accordance with the sanitation protocols, or area information corresponding to the physical position of the individual dispenser, identified by the dispenser identification data, and included in a database accessed by said computing device;

wherein the actuator device is a push button or lever accessible from the exterior of the automatic dispenser and mechanically connected to said dosing device; and wherein the electronic device is connected to a blocking mechanism and configured to block and/or unblock the actuator device depending on the information obtained through the user recognition device.

2. The dispenser according to claim 1 where the dispenser includes also a clock connected to the electronic device, and where the electronic device is also configured to further transmit temporary data linked to the user identification data.

3. The dispenser according to claim 1 where the user recognition device is a biometric detector selected amongst:
a fingerprint reader that ingrates a finger scan surface;
a facial recognition device;
a device for recognizing the geometry of the hand;
a voice recognition device;
a device for recognizing the shape of the retina;
a device for recognizing the shape of the iris.

4. The dispenser according to claim 1 where the user recognition device is an identifier device selected amongst:
a reader of identification cards;
a proximity detector of personal identification cards, chips or antennas;
a personal identification code insertion keypad.

5. The dispenser according to claim 1, where the communicator device is a wireless communicator device.

6. The dispenser according to claim 1, where the dispenser is used in a healthcare establishment, and the information being communicated between said computing device and said information emitter includes patient related information.

7. The dispenser according to claim 1, where the information being communicated between said computing device and said information emitter is adapted to the user identified by recognition device.

8. The dispenser according to claim 1, where the dispenser has two reservoirs of disinfectant gel and is configured so that when one of the reservoirs dries up the electronic device generates a warning signal and the dispensation from the other reservoir is initiated, while transmitting gel consumption data through the communicator device in real time to the remote computing device.

9. The dispenser according to claim 1, where the reservoir of disinfectant gel is flexible and where the actuator device includes a pressure surface that presses said flexible reservoir.

10. The dispenser according to claim 1, where the dosing device consists of a piston housing of a predefined dimension that is filled with disinfectant gel after each dispensation and that when the actuator device is operated collapses and empties through the dispensing nozzle.

11. The dispenser according to claim 1, where the dosing device consists of a valve that opens and closes the dispensing nozzle in a controlled manner, said valve being actuated by the actuator device, regulating the flow of dispensed disinfectant gel.

12. The dispenser according to claim 1, where the actuator device includes a motor controlled by the electronic device, and where the electronic device is configured to activate said actuator device in response to a detection obtained by the user recognition device.

13. The dispenser according to claim 1, where the information emitter is selected between a lighting signal, a screen and/or a loudspeaker.

* * * * *